(12) United States Patent
Riondel et al.

(10) Patent No.: US 10,000,439 B2
(45) Date of Patent: Jun. 19, 2018

(54) PROCESS FOR PRODUCING ALKYL ACRYLATE

(71) Applicant: Arkema France, Colombes (FR)

(72) Inventors: Alain F. Riondel, Saint Pathus (FR); Coralie Graire, Grezieu-la-Varenne (FR); Marc Esch, Theding (FR); Andre Levray, Porcelette (FR)

(73) Assignee: Arkema France, Colombes (FR)

( * ) Notice: Subject to any disclaimer, the term of this patent is extended or adjusted under 35 U.S.C. 154(b) by 0 days. days.

(21) Appl. No.: 14/650,906

(22) PCT Filed: Dec. 16, 2013

(86) PCT No.: PCT/FR2013/053083
§ 371 (c)(1),
(2) Date: Jun. 10, 2015

(87) PCT Pub. No.: WO2014/096648
PCT Pub. Date: Jun. 26, 2014

(65) Prior Publication Data
US 2015/0315120 A1     Nov. 5, 2015

(30) Foreign Application Priority Data

Dec. 17, 2012   (FR) .................... 12 62123

(51) Int. Cl.
| C07C 67/03 | (2006.01) |
| C07C 67/54 | (2006.01) |
| C07C 213/06 | (2006.01) |
| C07C 219/08 | (2006.01) |
| C07C 69/54 | (2006.01) |

(52) U.S. Cl.
CPC .............. *C07C 67/03* (2013.01); *C07C 67/54* (2013.01); *C07C 213/06* (2013.01); *Y02P 20/582* (2015.11)

(58) Field of Classification Search
CPC ....... C07C 67/03; C07C 69/54; C07C 213/06; C07C 67/54; C07C 219/08; Y02P 20/582
USPC .......................................................... 560/217
See application file for complete search history.

(56) References Cited

U.S. PATENT DOCUMENTS

| 6,977,310 B2 | 12/2005 | Ackermann et al. |
| 7,268,451 B2 | 9/2007 | Hertz et al. |
| 2005/0119500 A1 | 6/2005 | Ackermann et al. |

FOREIGN PATENT DOCUMENTS

| EP | 0 968 995 B1 | | 8/2002 |
| JP | 2005239564 | * | 9/2005 |
| JP | 2005239564 A2 | | 9/2005 |

OTHER PUBLICATIONS

English language translation of JP 2005239564, p. 1-27, obtained May 2016.*

(Continued)

*Primary Examiner* — Jafar Parsa
*Assistant Examiner* — Amy C Bonaparte
(74) *Attorney, Agent, or Firm* — Lynn B. Morreule

(57) ABSTRACT

The invention relates to the production of alkyl acrylate according to a continuous transesterification process. In one embodiment the process of the invention uses a simple column to purify a reaction mixture of acryl acrylate in one step yielding alkyl acrylate with a purity of greater than 99.8%.

10 Claims, 1 Drawing Sheet

(56) References Cited

OTHER PUBLICATIONS

Specification Sheet for butyl acrylate (sigma aldrich, downloaded from http://www.sigmaaldrich.com/catalog/product/aldrich/234923?lang=en&region=US on Aug. 21, 2017, p. 1).*
Specification Sheet for butyl methacrylate (sigma aldrich, downloaded from http://www.sigmaaldrich.com/catalog/product/aldrich/235865?lang=en&region=US on Aug. 21, 2017, p. 1).*

* cited by examiner

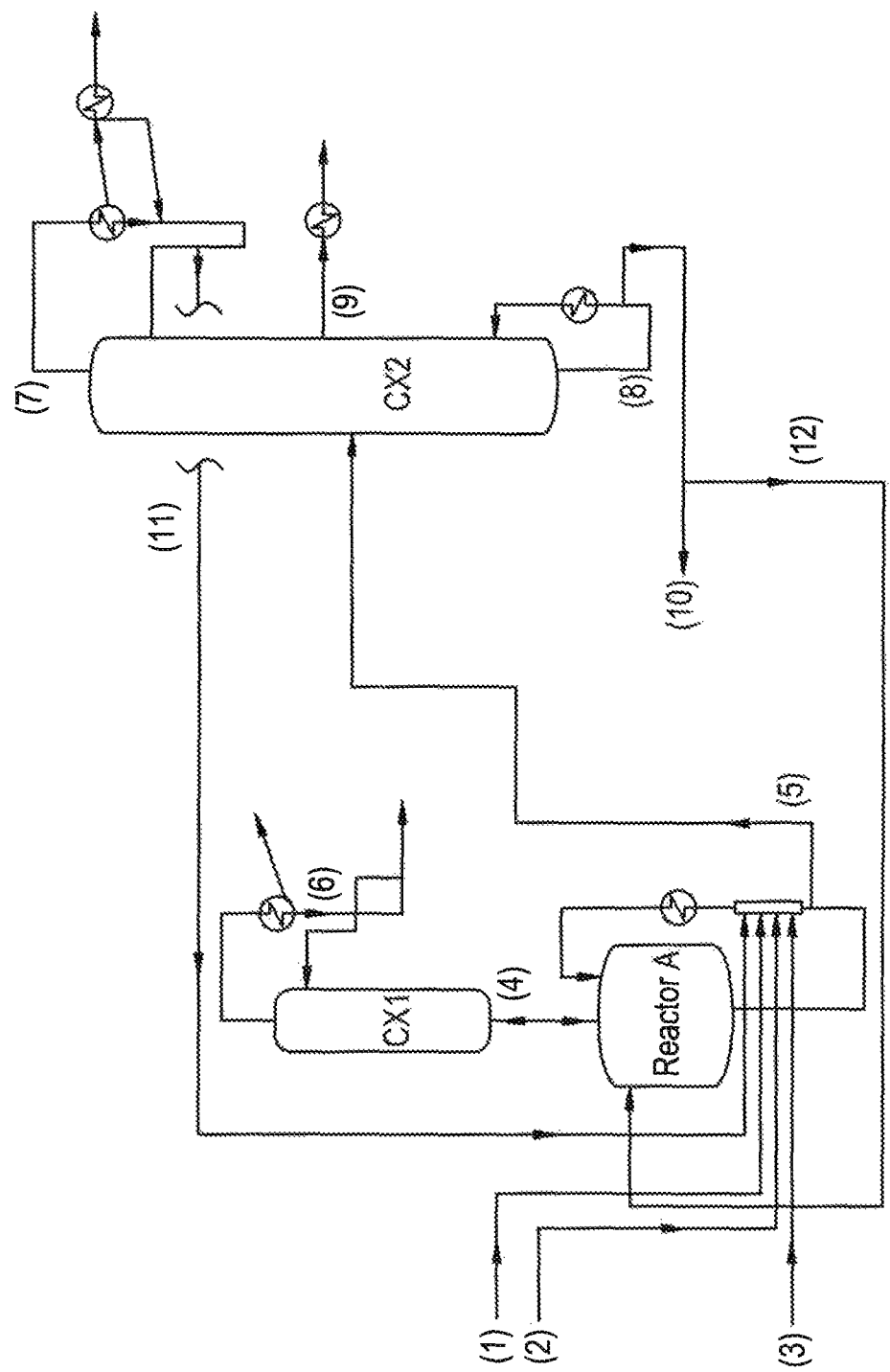

PROCESS FOR PRODUCING ALKYL ACRYLATE

CROSS-REFERENCE TO RELATED APPLICATIONS

This application is a national stage application under 35 U.S.C. § 371 of PCT/FR2013/053083, filed Dec. 16, 2013, which claims benefit to FR patent application FR 12.62123, filed Dec. 17, 2012.

FIELD OF THE INVENTION

The present invention relates to the production of alkyl acrylate according to a continuous transesterification process.

TECHNICAL BACKGROUND

The production of esters by transesterification has for decades been a broadly widespread reaction in the field of acrylics. Nonetheless, processing the crude reaction product and obtaining the desired product in a purified form present numerous technical challenges and have been the subject of numerous developments.

The transesterification reaction involves a "short" chain alkyl acrylate, referred to as being "light", in the presence of a "long" chain alcohol, referred to as being "heavy", generally in the presence of catalyst and polymerization inhibitor, according to the following general formula (1):

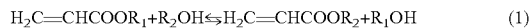
$$H_2C=CHCOOR_1 + R_2OH \leftrightarrows H_2C=CHCOOR_2 + R_1OH \quad (1)$$

In order to shift the equilibrium toward the formation of "long" chain alkyl acrylate, it is necessary to eliminate the "light" alcohol produced during the reaction. This reaction is generally accompanied by secondary reactions which produce impurities which must be eliminated with a view to obtaining the desired alkyl acrylate with a high enough level of purity to satisfy the technical requirements associated with its end use as monomer. The alkyl acrylate thus obtained is used in the production of (co)polymers which can be used in numerous fields of application.

Moreover, for obvious economic reasons, the exploitable products present in the crude reaction product mixture, notably unreacted reactants and catalyst, are recycled within the process as far as possible.

Alongside the recycling of exploitable products, the desired product needs to be isolated and purified. For this, numerous separation/purification processes comprising a set of distillations, extractions and/or settling operations are used.

For example, document U.S. Pat. No. 6,977,310 discloses processing the crude reaction product via a first distillation column which separates off the light products and sends the heavy products into a second column to separate the desired product from the catalyst and the polymerization inhibitors.

Document U.S. Pat. No. 7,268,251 discloses various ways of processing the crude reaction product comprising at least four distillation or rectification columns to purify the desired product, including an evaporator for separating off the catalyst.

The process described in document U.S. Pat. No. 7,268,251 has proved to be complicated to implement on an industrial scale due to the optimization of the operating conditions in the four successive distillation/rectification elements to obtain a product of high purity and a satisfactory productivity.

In document JP 2005-239564, use of a distillation column which uses "divided wall" technology (a divided wall column) is proposed to purify a reaction mixture of (meth) acrylic esters. This technology, based on the use of one sole column, nonetheless has drawbacks such as its cost compared to a conventional column (a dividing wall must be installed) and its lack of flexibility with regard to changing the type of streams to be processed.

Also known is document EP 0 968 995 which describes a process for producing alkyl acrylates and which discloses the use of a distillation column, in which the reactants and the desired product are recovered at the top in gaseous form and at the bottom in liquid form, respectively.

In addition, the transesterification reaction in this process occurs directly in the distillation column. The major drawbacks of using a homogeneous catalyst in a distillation column are the dramatic increase in the consumption thereof due to the reflux of the various effluents, and also, in the case of catalyst precipitation, fouling of the distillation column. In the case of a heterogeneous catalyst, the catalyst is located directly in the distillation column and cannot therefore be continuously recycled. Moreover, the efficiency of the catalyst, which decreases over time, directly impacts on the reaction yield. Replacing the catalyst represents a very high cost since the process must be stopped and the column completely cleaned between each catalyst loading.

Processing the crude reaction product derived from the transesterification reaction in the field of acrylics has been the subject of numerous developments. Nonetheless, these processes are still unsatisfactory. There is therefore a great need to be able to have a process for manufacturing alkyl acrylates which is simpler, has better performance, does not have the drawbacks of the prior art on an industrial scale and which meets the requirements of purity of the manufactured product associated with its end use for example as monomer for the manufacture of latex with a low content of volatile organic compounds.

After various experiments, the Applicant has found a process for the production of alkyl acrylate comprising processing the crude reaction mixture by distillation by means of a single simple column, which has never been suggested in the prior art.

According to the teaching of document JP 2005-239564, it is necessary to use a divided wall column to obtain a short chain alkyl (meth)acrylate with sufficient purity, such as butyl methacrylate. The Applicant has found numerous drawbacks to this use, since it is a column with a size generally very much larger than that of a conventional column, therefore with a higher cost, and the use thereof is difficult in terms of optimization of operation, of distribution of the polymerization inhibitors introduced, or of cleaning in the event of deposits on the walls.

Surprisingly, the Applicant has now discovered that using a simple column to purify a reaction mixture of alkyl acrylate in just one step makes it possible to obtain an alkyl acrylate with a purity of greater than 99.8%.

Using a simple column makes use of simplified technology which is more flexible and less costly than that used in document JP 2005-239564. Moreover, it is apparent to the Applicant that this process advantageously applies to the continuous production of heavy alkyl acrylates, that is to say with an alkyl chain comprising more than 4 carbon atoms.

This process makes it possible to both simplify and improve the processing of effluents compared to those of the prior art, to achieve a product of high purity and a high productivity.

Thus, by virtue of using a single simple distillation column for processing the crude reaction product, the process according to the invention makes possible a significant reduction in purification costs compared to those arising from the current processes.

SUMMARY OF THE INVENTION

The subject of the present invention is a process for the continuous production of alkyl acrylate by transesterification reaction between a light alkyl acrylate and a heavy alcohol in the presence of at least one catalyst and at least one polymerization inhibitor, represented by the following reaction:

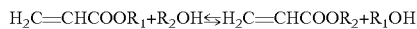

$$H_2C=CHCOOR_1+R_2OH \leftrightarrows H_2C=CHCOOR_2+R_1OH$$

in which reaction $R_1$ represents a methyl or ethyl group. $R_2$ represents a linear or branched alkyl group of between 4 and 9 carbon atoms, possibly comprising a nitrogen atom, said reaction being carried out in a reactor coupled to a distillation column, from which the azeotropic mixture composed of light alkyl acrylate and light alcohol generated by the transesterification reaction is drawn off continuously, characterized in that the crude reaction product comprising the unreacted reactants, the formed reaction products, the catalyst(s) and the polymerization inhibitor(s) is sent to a single distillation column under reduced pressure, in which the distillation makes it possible to obtain:
- at the top, a stream of light products essentially consisting of the residual alcohols $R_2OH$ and $R_1OH$ and also the unreacted reactant $H_2C=CHCOOR_1$, which is recycled to the reactor,
- in the bottom portion, the desired product $H_2C=CHCOOR_2$ which is drawn off laterally in the gas phase,
- at the bottom, a stream of heavy reaction products comprising the catalyst(s), the polymerization inhibitor(s) and $H_2C=CHCOOR_2$ which is recycled in part to the reactor.

According to one embodiment, the process according to the invention is characterized in that the transesterification catalyst is an alkyl titanate, preferably ethyl titanate and/or 2-octyl titanate in solution in 2-octanol.

According to a preferred possibility afforded by the invention, the process is characterized in that $R_2$ represents a linear or branched alkyl group of 8 carbon atoms, preferably 2-octyl.

According to one embodiment, the process according to the invention is characterized in that $R_1$ represents an ethyl group.

According to a preferred embodiment, the process according to the invention is characterized in that the catalyst is present in an amount of $5 \times 10^{-4}$ to $5 \times 10^{-2}$ mol per mole of $R_2OH$, preferably in an amount of $10^{-3}$ to $10^{-2}$ mol per mole of $R_2OH$.

According to a very particularly preferred possibility afforded by the invention, the process according to the invention is characterized in that it is suitable for the manufacture of 2-octyl acrylate, for which ethyl titanate and/or 2-octyl titanate in 2-octanol will be used as catalyst.

Preferably, the process according to the invention is characterized in that the molar ratio of the compound $H_2C=CHCOOR_1$ and of the compound $R_2OH$ is between 1 and 3, preferably between 1.3 and 1.8.

According to a very particularly preferred embodiment, the process according to the invention is characterized in that the transesterification reaction is carried out at a pressure of between 350 mmHg (or $0.47 \times 10^5$ Pa) and atmospheric pressure (760 mmHg, or $10^5$ Pa), and at a temperature of between 90° C. and 150° C., preferably 100° C. to 130° C.

The invention will now be described in more detail in the following description, with reference to the single appended FIGURE which schematically shows a facility for implementing the process of the invention.

BRIEF DESCRIPTION OF THE FIGURE

The invention is best understood from the following detailed description when read in connection with the accompanying FIGURE.

The FIGURE depicts an operating example of the process according to the invention.

DETAILED DESCRIPTION

In general, the light alkyl acrylate reactant is chosen from methyl acrylate or ethyl acrylate, more preferably ethyl acrylate.

According to a very particularly beneficial embodiment of the process of the invention, the starting materials are of natural, renewable origin, that is to say they are bio-based. For example, the 2-octanol may be obtained by alkaline treatment of ricinoleic acid derived from castor oil.

More particularly, the light alkyl acrylate may be derived from acrylic acid of renewable origin, possibly being in particular obtained from glycerol, according to a process comprising a first step of dehydrating the glycerol to give acrolein, followed by a step of gas-phase oxidation of the acrolein thus obtained; or may be obtained by dehydrating 2-hydroxypropionic acid (lactic acid) or 3-hydroxypropionic acid and their esters.

The heavy alcohol reactant $R_2OH$ is a primary or secondary alcohol with a linear or branched alkyl chain comprising from 4 to 9 carbon atoms, preferably from 5 to 9 carbon atoms, and possibly comprising a nitrogen atom.

In general, the reactant $R_2OH$ may be chosen, without this list being limiting, from butan-1-ol, butan-2-ol, isobutanol, penton-1-ol (amyl alcohol), 2,2-methylpropan-1-ol (isoamyl alcohol), hexan-1-ol, benzyl alcohol, 1-octanol, 2-octanol, 2-ethylhexanol, 1-nonanol, N,N-dimethylaminoethanol and N,N-diethylaminoethanol.

Preferably, the alcohol is chosen from 2-octanol, 2-ethylhexanol and N,N-dimethylaminoethanol.

More preferably, the reactant $R_2OH$ is 2-octanol.

The catalyst is chosen from all catalysts with the capacity to catalyze the transesterification reaction between a light alkyl acrylate and a heavy alcohol, for example acids such as sulfuric acid and p-toluenesulfonic acid; basic compounds such as alkoxides, hydroxides, carbonates, phosphates, oxides or complexes of alkali metals or alkaline earth metals; metal alkoxide complexes such as aluminum alkoxide or magnesium alkoxide; titanium-based compounds such as titanium alkoxides, titanium phenoxides or alkyl titanates; compounds based on lead, zinc or tin; copper, iron or zirconium complexes.

More particularly, the catalyst according to the process of the invention is chosen from an alkyl titanate of formula $Ti(OR_1)_4$ or $Ti(OR_2)_4$ in solution in alcohol $R_1OH$ and/or $R_2OH$, for example a solution of 80 to 90% ethyl titanium in alcohol $R_2OH$ or ethanol, and/or the $R_2OH$ titanate in alcohol $R_2OH$. It is understood that the alcohol used to place the catalyst in solution is the same as that used or generated in the transesterification reaction.

More preferably, 2-octyl titanate in solution in 2-octanol, obtained beforehand by reacting ethyl titanate or isopropyl titanate with 2-octanol at 100° C., is used.

The reaction is carried out in the presence of one or more polymerization inhibitors which are introduced into the reactor in an amount of 1000 to 5000 ppm relative to the crude reaction product mixture. As polymerization inhibitors which may be used, mention may be made for example of phenothiazine, hydroquinone, hydroquinone monomethyl ether, di-tert-butyl para-cresol (BHT), TEMPO (2,2,6,6-tetramethyl-1-piperidinyloxy), di-tert-butylcatechol, or TEMPO derivatives such as 4-hydroxy(OH)-TEMPO, on their own or mixtures thereof in any proportions. A supplementary addition of polymerization inhibitor is generally carried out during the subsequent purification processing, in particular at the distillation column.

The single distillation column processing the crude reaction product according to the process of the invention is a simple distillation column, for example a column with structured packing or a plate column, generally comprising between 15 and 20 theoretical plates, for example 18 theoretical plates, the pressure of which may be adjusted to the desired level, optionally protected by thermal insulation, and optionally fitted with access devices for maintenance operations.

Within the context of the present invention, the term simple distillation column is intended to mean a column containing distillation plates with or without downcomers, or containing packing of the random or structured type, optionally with recentering plates for the distribution of liquid, able to operate at pressures below atmospheric pressure. This column is fitted with a system enabling the product to be drawn off as vapor, in the lateral position of said column, and does not comprise a vertical dividing wall.

An operating example of the process according to the invention is now described with reference to the appended FIGURE.

The light alcohol ($R_1OH$) formed in the reactor by the transesterification reaction between a light alkyl acrylate (3) and a heavy alcohol (1) in the presence of catalyst (2) is continuously fed (4) into a distillation column (CX1) on top of the reactor (A) in the form of an azeotropic mixture with the light alkyl acrylate (3). The azeotropic mixture may be used in a unit for synthesizing light ester (6).

After reaction, according to a residence time in the reactor of generally between 3 and 6 hours, the crude reaction product mixture (5) contains the desired alkyl acrylate with as light products the heavy alcohol ($R_2OH$) and the unreacted light alkyl acrylate, and as heavy compounds the catalyst, the polymerization inhibitor(s) and heavy by-products of the reaction.

The crude reaction product mixture (5) undergoes purification processing in a single distillation column (CX2) in order to obtain on the one hand the pure desired alkyl acrylate (9) which is drawn off laterally, and on the other hand, at the top of the column, the residual alcohols ($R_2OH$ and $R_2OH$) and the light alkyl acrylate which have not reacted (7) and are intended to be recycled (11), and at the bottom of the column, catalyst, polymerization inhibitor, heavy by-products of the reaction and the heavy ester (8) which are intended to be recycled in part (12) to the reactor (A), with the other part being sent (10):
- either to a film evaporator (not shown on the diagram) to recover an overhead stream containing the desired alkyl acrylate and a bottoms stream which is sent to a destruction facility,
- or to a destruction facility.

The column (CX2) is a simple distillation column operating under reduced pressure, preferably corresponding to a column with structured packing or a plate column comprising between 15 and 20 theoretical plates, preferably 18 theoretical plates, operating under reduced pressure.

Preferably, the distillation column processing the crude reaction product operates at a pressure of between 20 and 150 mmHg (or between $0.027 \times 10^5$ Pa and $0.2 \times 10^5$ Pa), preferably between 20 and 75 mmHg (or between $0.027 \times 10^5$ Pa and $0.1 \times 10^5$ Pa).

Preferably, the desired alkyl acrylate is drawn of laterally in the gas phase in the bottom portion of the distillation column, between theoretical plates 12 and 14 for a column with 18 theoretical plates.

The process according to the invention makes it possible to produce the desired product, i.e. alkyl acrylate, with a purity of greater than 99.8%.

The following concrete but nonlimiting examples are given in order to illustrate and better understand the invention.

EXPERIMENTAL SECTION

In the examples, the percentages are given by weight unless indicated otherwise, and the following abbreviations have been used:
EA: ethyl acrylate
2OCTA: 2-octyl acrylate
PTZ: phenothiazine
HQME: hydroquinone methyl ester
Example Ethyl acrylate (3), 2-octanol (1) and a mixture of ethyl titanate (2) in solution in 2-octanol (90% mixture of ethyl titanate in 2-octanol) with phenothiazine inhibitor, in proportions by weight of 50.1/49.7/0.2, are fed to a perfectly stirred reactor A heated by an external exchanger and with an distillation column (CX1) on top, with 12 theoretical plates.

The reactor is heated with air bubbling and as soon as the temperature reaches 125° C. under 640 millibar, the EA (3) stabilized with 2000 ppm of PTZ, the 2-octanol (1) and the ethyl titanate in solution in 2-octanol (2) are introduced continuously in proportions by weight of 50.1/49.7/0.2.

At the top of the column (CX1), the EA/ethanol azeotrope (4), with a composition by weight of 40/60, is drawn off continuously. This mixture (4) is recycled to the light ester facility.

The crude reaction product (5), obtained by continuous reaction, contains 2OCTA, unreacted EA, unreacted 2-octanol and a mixture comprising the catalyst with the polymerization inhibitors and heavy derivatives.

The stream (5) is continuously sent to a single distillation column (CX2) with 18 theoretical plates operating under reduced pressure and heated by an external exchanger to a temperature of 140° C.

At the top of the column (CX2), a mixture of 2500 ppm PTZ in EA (not shown in the FIGURE) is introduced.

The column CX2 separates, at the top, a mixture (7) of EA/2-octanol/2OCTA with a composition of 52.4/34.2/4.6 which is recycled (11) to the reactor (A), and at the bottom, a mixture (8) comprising a mixture of heavy products, polymerization inhibitors and catalyst with a 2OCTA fraction with a proportion by weight of 15.9/84.1, which is recycled in part to the reaction (12), and the other part is send to the heavy processing section (10).

Pure 2-octyl acrylate (9) is obtained by laterally drawing off in the gas phase in the bottom portion of the column at plate no. 13. The purity of the 2-octyl acrylate is 99.89%.

The invention claimed is:

1. A process for the continuous production of alkyl acrylates, by a transesterification reaction between a light alkyl acrylate and a heavy alcohol in the presence of at least one catalyst and at least one polymerization inhibitor, said transesterification reaction represented by the reaction:

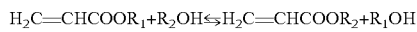

wherein $R_1$ is a methyl or ethyl group, $R_2$ is a linear or branched alkyl group having 4 to 9 carbon atoms, and optionally comprising a nitrogen atom, carrying out said reaction in a reactor coupled to a distillation column from which an azeotropic mixture comprising light alkyl acrylate and light alcohol generated by the transesterification reaction is drawn off, sending a crude reaction product comprising unreacted reactants, formed reaction products, catalyst(s) and polymerization inhibitor(s) to a single distillation column which is a simple column lacking a vertical divided wall and under reduced pressure for distillation, whereby the distillation yields:

at a top portion, a stream of light products consisting essentially of residual alcohols $R_2OH$ and $R_1OH$ and unreacted reactant $H_2C=CHCOOR_1$, which is recycled to the reactor, in a bottom portion, product $H_2C=CHCOOR_2$ which is drawn off laterally in a gas phase, at a bottom, a stream of heavy reaction products comprising the catalyst(s), the polymerization inhibitor(s) and $H_2C=CHCOOR_2$ which is recycled in part to the reactor;

such that said process produces said alkyl acrylates have a purity greater than 99.8%.

2. The process as claimed in claim 1, wherein the single distillation column processing the crude reaction product is a simple column containing distillation plates with or without downcomers, or containing packing of random or structured type, optionally with recentering plates for the distribution of liquid, able to operate at pressures below atmospheric pressure.

3. The process as claimed in claim 1 wherein the alcohol $R_2OH$ is selected from the group consisting of 2-octanol, 2-ethylhexanol and N,N-dimethylaminoethanol.

4. The process as claimed in claim 3 wherein the alcohol is 2-octanol.

5. The process as claimed in claim 1 wherein the transesterification catalyst is an alkyl titanate of formula $Ti(OR_1)_4$ or $Ti(OR_2)_4$ in solution in the alcohol $R_1OH$ and/or $R_2OH$.

6. The process as claimed in claim 1 wherein $R_1$ is an ethyl group.

7. The process as claimed in claim 1 wherein the catalyst is present in an amount of $5 \times 10^{-4}$ to $5 \times 10^{-2}$ mol per mole of $R_2OH$.

8. The process as claimed in claim 1 wherein compound $H_2C=CHCOOR_1$ and the compound $R_2OH$ have a molar ratio between 1 and 3.

9. The process as claimed in claim 1 wherein the transesterification reaction is carried out at a pressure between 350 mmHg ($0.47 \times 10^5$ Pa) and atmospheric pressure, and at a temperature between 90° C. and 150° C.

10. The process as claimed in claim 1 for the manufacture of 2-octyl acrylate, using ethyl titanate and/or 2-octyl titanate in 2-octanol as the catalyst.

* * * * *